(12) United States Patent
Hoshi

(10) Patent No.: US 6,197,727 B1
(45) Date of Patent: Mar. 6, 2001

(54) HERBICIDE COMPOSITIONS

(75) Inventor: Hisayuki Hoshi, Toyonaka (JP)

(73) Assignee: Sumitomo Chemical Company, Limited, Osaka-Fu (JP)

( * ) Notice: Subject to any disclaimer, the term of this patent is extended or adjusted under 35 U.S.C. 154(b) by 0 days.

(21) Appl. No.: 09/367,357

(22) PCT Filed: Feb. 17, 1998

(86) PCT No.: PCT/JP98/00634

§ 371 Date: Aug. 12, 1999

§ 102(e) Date: Aug. 12, 1999

(87) PCT Pub. No.: WO98/36642

PCT Pub. Date: Aug. 27, 1998

(30) Foreign Application Priority Data

| Feb. 19, 1997 | (JP) | 9-035390 |
| Feb. 19, 1997 | (JP) | 9-035391 |
| Feb. 19, 1997 | (JP) | 9-035392 |
| Feb. 19, 1997 | (JP) | 9-035393 |
| Feb. 20, 1997 | (JP) | 9-036694 |
| Feb. 20, 1997 | (JP) | 9-036695 |

(51) Int. Cl.$^7$ ..................................... A01N 43/58
(52) U.S. Cl. .............................. 504/134; 504/137
(58) Field of Search ..................... 504/134, 137

(56) References Cited

FOREIGN PATENT DOCUMENTS

96/39392  12/1996  (WO) ................... C07D/237/14

Primary Examiner—S. Mark Clardy
(74) Attorney, Agent, or Firm—Sughrue, Mion, Zinn, Macpeak & Seas, PLLC

(57) ABSTRACT

The present invention provides herbicide compositions for foliar treatment each containing as active ingredients, a 2-chloro-4-fluoro-5-(4methyl-5-trifluoromethyl-3-pyridazinon-2-chloro-2-yl)phenyl $C_1$–$C_5$ non-cyclic hydrocarbyl ether and one selected from the group consisting of (RS)-2-(4-chloro-2methylphenoxy)propionic acid, 2,4-dichlorophenoxyacetic acid, (4-chloro-2-methyl)phenoxyacetic acid, 2-[[[[(4-methoxy-6-methyl-1,3,5-triazin-2-yl)-amino]carbonyl]amino]sulfonyl] benzoate, 2-chloro-N-[[(4-methoxy-6-methyl-1,3,5-triazin-2-yl)amino]carbonyl]benzenesulfonamide, ethyl (R)-2-[4(6-chloro-1 3-benzoxazol-2-yloxy)phenoxy]propanoate, methyl (RS)-2-[4-(2,4-dichlorophenoxy)phenoxy]propionate, 3,5-dibromo-4-hydroxybenzonitrile, 4-hydroxy-3,5-diiodobenzonitrile, 3-(4-isopropylphenyl)-N', N'-dimethylurea, N'-(3-chloro-4-methylphenyl)-N,N-dimethylurea and N-(2,4-difluorophenyl)-2-[3-(trifluoromethyl)phenoxy]-3-pyridinecarboxamide; and a weeding method by foliar treatment of weeds therewith.

The present compositions can be used for effective control of various weeds occurring on crop lands or non-crop lands, in which case the herbicidal activity is synergistically enhanced as compared with the cases where the active ingredients are used separately, which makes possible low-dose application, and the herbicidal spectra are expanded, so that a wide variety of weeds can be selectively controlled, particularly on wheat, barley, oat, or rye fields.

45 Claims, No Drawings

HERBICIDE COMPOSITIONS

TECHNICAL FIELD

The present invention relates to herbicide compositions, and more particularly, it relates to herbicide compositions for foliar treatment and a weeding method by foliar treatment of weeds therewith.

BACKGROUND ART

At present, a great number of herbicides are commercially available and used. There are, however, many kinds of weeds to be controlled and their occurrence extends over a long time. For this reason, requested are herbicides having higher herbicidal activity, wide herbicidal spectra and safety on crops.

DISCLOSURE OF THE INVENTION

The present inventor has extensively studied to find out excellent herbicides. As a result, he has found that various weeds occurring on crop lands or non-crop lands can be effectively controlled by foliar treatment of these weeds with a herbicide composition comprising as active ingredients, a 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of (RS)-2-(4-chloro-2-methylphenoxy)propionic acid (common name, mecoprop; hereinafter referred to as mecoprop), 2,4-dichlorophenoxyacetic acid (common name, 2,4-D; hereinafter referred to as 2,4-D), (4-chloro-2-methyl) phenoxyacetic acid (common name, MCPA; hereinafter referred to as MCPA), 2- [[[[(4-methoxy-6-methyl-1,3,5-triazin-2-yl)-amino]carbonyl]-amino]sulfonyl] benzoate (common name, metsulfuron-methyl; hereinafter referred to as metsulfuron-methyl), 2-chloro-N-[[(4-methoxy-6-methyl-1,3,5-triazin-2-yl)amino]carbonyl] benzenesulfonamide (common name, chlorsulfuron; hereinafter referred to as chlorsulfuron), ethyl (R)-2-[4-(6-chloro-1,3-benzoxazol-2-yloxy)phenoxy]propanoate (common name, fenoxaprop-P-ethyl; hereinafter referred to as fenoxaprop-P-ethyl), methyl (RS)-2-[4-(2,4-dichlorophenoxy)phenoxy]propionate (common name, dichlofop-methyl; hereinafter referred to as dichlofop-methyl), 3,5-dibromo-4-hydroxybenzonitrile (common name, bromoxynil; referred to as bromoxynil), 4-hydroxy-3,5-diiodobenzonitrile (common name, ioxynil; referred to as ioxynil), 3-(4-isopropylphenyl)-N',N'-dimethylurea (common name, isoproturon; hereinafter referred to as isoproturon), N'-(3-chloro-4-methylphenyl)-N,N-dimethylurea (common name, chlorotoluron; hereinafter referred to as chlorotoluron) and N-(2,4-difluorophenyl)-2-[3-(trifluoromethyl)phenoxy]-3-pyridinecarboxamide (common name, diflufenican; hereinafter referred to as diflufenican), in which case the herbicidal activity is synergistically enhanced as compared with the cases where the active ingredients are used separately, which makes possible low-dose application; and the herbicidal spectra are expanded, so that a wide variety of weeds can be controlled, particularly on wheat, barley, oat, or rye fields without exhibiting material phytotoxicity on wheat, barley, oat, or rye, thereby completing the present invention.

Thus, the present invention provides herbicide compositions (hereinafter referred to as the present compositions) each comprising as active ingredients, a 2-chloro-4-fluoro-5-(4-methyl-5-trifluoromethyl-3-pyridazinon-2-yl)phenyl $C_1$–$C_5$ non-cyclic hydrocarbyl ether ( hereinafter referred to as the ether compound) and one (hereinafter referred to as component (a)) selected from the group consisting of mecoprop, 2,4-D, MCPA, metsulfuron-methyl, chlorsulfuron, fenoxaprop-P-ethyl, dichlofop-methyl, bromoxynil, ioxynil, isoproturon, chlorotoluron and diflufenican; and a weeding method by foliar treatment of weeds therewith.

The $C_1$–$C_5$ non-cyclic hydrocarbyl in the ether compound, which is one of the active ingredients of the present compositions, refers to, for example, 2-propynyl, 1-methyl-2-propynyl, allyl, 1-methylallyl, isopropyl or ethyl. These compounds can be produced by the processes as shown in the following Production Examples.

PRODUCTION EXAMPLE 1

To a solution of 5.3 g (53.3 mmol) of sodium acetate mixed with about 100 ml of water was added under ice cooling 6.6 g (24.3 mmol) of 1,1-dibromo-3,3,3-trifluoroacetone, and the mixture was stirred at 70° C. for 20 minutes. The reaction mixture was cooled to room temperature, to which a solution of 5.8 g (21.5 mmol) of 2-fluoro-4-chloro-5-isopropoxy-phenylhydrazine dissolved in about 20 ml of diethyl ether was added, and the mixture was stirred at room temperature for 1 hour. The ether layer was separated and concentrated. The residue was mixed with about 60 ml of THF, to which 8.3 g (23.0 mmol) of carboethoxyethylidenetriphenylphosphorane was added, and the mixture was heated under reflux for 2 hours. The THF was distilled out under reduced pressure, and the residue was subjected to silica gel column chromatography to give 3.8 g (10.5 mmol) of 2-[2-fluoro-4-chloro-5-isopropoxyphenyl]-4-methyl-5-trifluoromethylpyridazin-3-one.

Then, 3.5 g (9.7 mmol) of 2-[2-fluoro-4-chloro-5-isopropoxyphenyl]-4-methyl-5-trifluoromethylpyridazin-3-one was dissolved in about 10 ml of concentrated sulfuric acid under ice cooling, and the solution was warmed to room temperature. After 10 minutes, about 100 ml of water was added to the reaction mixture. The precipitated crystals were collected by filtration and washed twice with 20 ml of water and then once with 10 ml of hexane. The resulting crystals were recrystallized from isopropanol to give 3.2 g (9.9 mmol) of 2-[2-fluoro-4-chloro-5-hydroxyphenyl]-4-methyl-5-trifluoromethylpyridazin-3-one.

Then, 3.2 g of 2-[2-fluoro-4-chloro-5-hydroxyphenyl]-4-methyl-5-trifluoromethylpyridazin-3-one was dissolved in about 50 ml of DMF, to which 2.0 g of potassium carbonate was added at room temperature. Furthermore, 1.3 g of propargyl bromide was added, and the mixture was stirred at room temperature for 30 minutes. The reaction mixture was mixed with 100 m of water, and the precipitated crystals were collected by filtration and washed with hexane. The resulting crystals were recrystallized from isopropanol to give 3.4 g of 2-[2-fluoro-4-chloro-5-(2-propynyloxy) phenyl]-4-methyl-5-trifluoromethylpyridazin-3-one (hereinafter referred to as compound A) (m.p., 140.7° C.; decomposition).

PRODUCTION EXAMPLE 2

The same procedures as described above in Production Example 1 are repeated, except that the following reagents are substituted for propargyl bromide, in which cases the desired ether compounds can be obtained.

TABLE 1

| Reagent | Hydrocarbyl of ether compound produced | Compound symbol | Physical property (m.p., °C.) |
| --- | --- | --- | --- |
| 3-bromo-1-butyn | 1-methyl-2-propynyl | B | 114.1 |
| allyl bromide | allyl | C | 79.8 |
| 3-bromo-1-butene | 1-methylallyl | D | |
| ethyl bromide | ethyl | E | |
| isopropyl bromide | isopropyl | F | |

$^1$H-NMR (300 MHz, CDCl$_3$, TMS, δppm)): Compound E 1.46 (3 H, t, J=5.8 Hz), 2.44 (3 H, q, J=1.5 Hz), 4.07 (2 H, q, J=5.8 Hz), 6.94 (1 H, d, J=5.0 Hz), 7.29 (1 H, d, J=7.5 Hz), 8.01 (1 H, s) Compound F 1.38 (6 H, d, J=6.3 Hz), 2.43 (3 H, q, J=2.0 Hz), 4.47 (1 H, m), 6.99 (1 H, d, J=5.0 Hz), 7.29 (1 H, d, J=9.5 Hz), 8.00 (1 H, s)

Mecoprop is the compound described in Farm Chemicals Handbook, 1995 (published by Meister, Publishing Co., 1995), page C236.

2,4-D is the compound described in Farm Chemicals Handbook, 1995 (published by Meister, Publishing Co., 1995), page C111.

MCPA is the compound described in Farm Chemicals Handbook, 1995 (published by Meister, Publishing Co., 1995), page C233.

Mecoprop, 2,4-D and MCPA can also be used in the form of agriculturally acceptable salts. In the present specification, mecoprop, 2,4-D and MCPA encompass their salts. The salts of these compounds may include alkali metal salts, alkaline earth metal salts; amine salts such as isopropylamine salts, dimethylamine salts and diglycolamine salts; and ammonium salts.

Metsulfuron-methyl is the compound described in Farm Chemicals Handbook, 1995 (published by Meister, Publishing Co., 1995), page C249.

Chlorsulfuron is the compound described in Farm Chemicals Handbook, 1995 (published by Meister, Publishing Co., 1995), page C88.

Fenoxaprop-P-ethyl is the compound described in Farm Chemicals Handbook, 1995 (published by Meister, Publishing Co., 1995), page C164.

Dichlofop-methyl is the compound described in Farm Chemicals Handbook, 1995 (published by Meister, Publishing Co., 1995), page C201.

Bromoxynil is the compound described in Farm Chemicals Handbook, 1995 (published by Meister, Publishing Co., 1995), page C61.

Ioxynil is the compound described in Farm Chemicals Handbook, 1995 (published by Meister, Publishing Co., 1995), page C209.

Isoproturon is the compound described in Farm Chemicals Handbook, 1995 (published by Meister, Publishing Co., 1995), page C211.

Chlorotoluron is the compound described in Farm Chemicals Handbook, 1995 (published by Meister, Publishing Co., 1995), page C86.

Diflufenican is the compound described in Farm Chemicals Handbook, 1995 (published by Meister, Publishing Co., 1995), page C128.

The present invention provides herbicidal compositions which may be effective for controlling a wide variety of weeds selectively from crops or for application to new cultivation methods such as non-tillage cultivation. The present compositions can attain effective control of typical weeds on wheat, barley, oat, or rye fields, for example, dicotyledons such as common chickweed (*Stellaria media*), catchweed bedstraw (*Galium aparine*), Persian speedwell (*Veronica persica*), ivyleaf speedwell (*Veronica hederifolia*), violet (*Viola mandshurica*), purple deadnettle (*Lamium purpureum*), henbit (*Lamium amplexicaure*), shepherdspurse (*Capsella bursa-pastoris*), annual sowthistle (*Sonchus oleraceus*), scentless chamomile (*Matricaria perforata*), wild mustard (*Sinapis arvensis*), forget-me-not (*Myosotis alpestris*), smartweed (*Polygonum hydropiper*), common lambsquarters (*Chenopodium album*), kochia (*Kochia scoparia*) and slender amaranth (*Amaranthus gracilis*); and monocotyledons such as barnyardgrass (*Echinochloa crus-gail*), green foxtail (*Setaria viridis*), annual bluegrass (*Poa annua*), blackgrass (*Alopecurus myosuroides*), Italian ryegrass (*Lolium multiflorum*), downy brome (*Bromus tectorum*) and wild oats (*Avena fatua*); however, they exhibit no material phytotoxicity on wheat, barley, oat, or rye as a crop and on corn as a succeeding crop.

In the present compositions, the mixing ratio of the ether compound and component (a) as the active ingredients, although it may vary with the kinds of weeds to be controlled, occasions and conditions of application, and other factors, is usually in the range of 1:5 to 1000 by weight ratio when component (a) is one selected from the group consisting of mecoprop, 2,4-D and MCPA; usually in the range of 1:0.05 to 5 by weight ratio when component (a) is one selected from the group consisting of metsulfuronmethyl and chlorsulfuron; usually in the range of 1:0.5 to 1000 by weight ratio when component (a) is one selected from the group consisting of fenoxaprop-P-ethyl and diclofopmethyl; usually in the range of 1:0.6 to 200, practically preferably 1:2 to 200 by weight ratio when component (a) is one selected from the group consisting of bromoxynil and ioxynil; usually in the range of 1:10 to 2000 by weight ratio when component (a) is one selected from the group consisting of isoproturon and chlorotoluron; and usually in the range of 1:1 to 100 by weight ratio when component (a) is diflufenican.

The present compositions are usually used in the form of formulations, for example, emulsifiable concentrates, wettable powders or flowables, which can be prepared by mixing these compositions with solid carriers, liquid carriers or others, and if necessary, adding surfactants or other adjuvants to the mixture. In these formulations, the ether compound and component (a) are usually contained in the total amount of 0.5% to 90% by weight, preferably 1% to 80% by weight.

The solid carriers used in the formulation may include, for example, finely powdered or granular materials of clays (e.g., kaolinite, diatomaceous earth, synthetic hydrated silicon oxide, Fubasami clay, bentonite, acid clay); talc and other inorganic minerals (e.g., sericite, powdered quartz, powdered sulfur, activated carbon, calcium carbonate); and chemical fertilizers (e.g., ammonium sulfate, ammonium phosphate, ammonium nitrate, ammonium chloride, urea). The liquid carriers may include, for example, water; alcohols (e.g., methanol, ethanol); ketones (e.g., acetone, methyl ethyl ketone, cyclohexanone); aromatic hydrocarbons (e.g., toluene, xylene, ethylbenzene, methylnaphthalene); nonaromatic hydrocarbons (e.g., hexane, cyclohexane, kerosine); esters (e.g., ethyl acetate, butyl acetate); nitrites (e.g., acetonitrile, isobutyronitrile); ethers (e.g., dioxane, diisopropyl ether); acid amides (e.g., dimethylformamide, dimethylacetamide); and halogenated hydrocarbons (e.g., dichloroethane, trichloroethylene).

The surfactants may include, for example, alkylsulfate esters; alkylsulfonate salts; alkylarylsulfonate salts; alkyl aryl ethers and their polyoxyethylene derivatives; polyethylene glycol ethers; polyhydric alcohol esters; and sugar alcohol derivatives.

The other adjuvants may include, for example, adhesive agents and dispersing agents, such as casein, gelatin, polysaccharides (e.g., powdered starch, gum arabic, cellulose derivatives, alginic acid), lignin derivatives, bentonite and synthetic water-soluble polymers (e.g., polyvinyl alcohol, polyvinyl pyrrolidone, polyacrylic acid); and stabilizers such as PAP (isopropyl acid phosphate), BHT (2,6-tert-butyl-4-methylphenol), BHA (2-/3-tert-butyl4-methyoxyphenol), vegetable oils, mineral oils, fatty acids and fatty acid esters.

The present compositions can also be prepared by separately making the active ingredients into the respective formulations according to the above formulation technique and then mixing these formulations.

The present compositions thus formulated may be applied to soil or plants as such or after diluted with water or others. The present compositions may also be used in admixture with other herbicides, in which case the herbicidal activity can be expected to be enhanced. The present compositions can also be used together with insecticides, bactericides, fungicides, plant growth regulators, fertilizers, soil conditioners or other agents.

The application amounts of the present compositions, although they may vary with the mixing ratio of the ether compound and component (a) as the active ingredient compounds, weather conditions, formulation types, application times, application methods, application places, weeds to be controlled, and crops to be protected, are usually in the range of 2 to 2500 g as the total amount of active ingredient compounds per hectare when component (a) is one selected from the group consisting of mecoprop, 2,4-D and MCPA; usually in the range of 2 to 100 g as the total amount of active ingredient compounds per hectare when component (a) is one selected from the group consisting of metsulfuron-methyl and chlorsulfuron; usually in the range of 2 to 1000 g as the total amount of active ingredient compounds per hectare when component (a) is one selected from the group consisting of fenoxaprop-P-ethyl and diclofop-methyl; usually in the range of 2 to 500 g as the total amount of active ingredient compounds per hectare when component (a) is one selected from the group consisting of bromoxynil and ioxynil; usually in the range of 2 to 2500 g as the total amount of active ingredient compounds per hectare when component (a) is one selected from the group consisting of isoproturon and chlorotoluron; usually in the range of 2 to 200 g as the total amount of active ingredient compounds per hectare when component (a) is diflufenican. In the cases of emulsifiable concentrates, wettable powders, flowables or other similar formulations, they are usually applied after diluted in their prescribed amounts with water at a ratio of 100 to 1000 liters per hectare.

The following will describe Formulation Examples. In the following Examples, the term "parts" represents parts by weight.

FORMULATION EXAMPLE 1

A wettable powder is prepared by well pulverizing and mixing 1 part of compound A, B, C, D, E or F, 50 parts of mecoprop, 3 parts of calcium lignin sulfonate, 2 parts of sodium lauryl sulfate and 44 parts of synthetic hydrated silicon oxide.

FORMULATION EXAMPLE 2

A wettable powder is prepared by well pulverizing and mixing 7 parts of compound A, B, C, D, E or F. 70 parts of mecoprop, 3 parts of calcium lignin sulfonate, 2 parts of sodium lauryl sulfate and 18 parts of synthetic hydrated silicon oxide.

FORMULATION EXAMPLE 3

A flowable is prepared by mixing 1 part of compound A, B, C, D, E or F, 50 parts of mecoprop, 3 parts of polyoxyethylene sorbitan monooleate, 3 parts of CMC (carboxymethylcellulose) and 43 parts of water, followed by pulverization until the particle size reaches 5 microns or smaller.

FORMULATION EXAMPLE 4

A flowable is prepared by mixing 7 parts of compound A, B, C, D, E or F, 70 parts of mecoprop, 3 parts of polyoxyethylene sorbitan monooleate, 3 parts of CMC (carboxymethylcellulose) and 17 parts of water, followed by pulverization until the particle size reaches 5 microns or smaller.

FORMULATION EXAMPLE 5

A wettable powder is prepared by well pulverizing and mixing 1 part of compound A, B, C, D, E or F. 50 parts of 2,4-D, 3 parts of calcium lignin sulfonate, 2 parts of sodium lauryl sulfate and 44 parts of synthetic hydrated silicon oxide.

FORMULATION EXAMPLE 6

A wettable powder is prepared by well pulverizing and mixing 13 parts of compound A, B, C, D, E or F, 65 parts of 2,4-D, 3 parts of calcium lignin sulfonate, 2 parts of sodium lauryl sulfate and 17 parts of synthetic hydrated silicon oxide.

FORMULATION EXAMPLE 7

A flowable is prepared by mixing 1 part of compound A, B, C, D, E or F, 50 parts of 2,4-D, 3 parts of polyoxyethylene sorbitan monooleate, 3 parts of CMC (carboxymethylcellulose) and 43 parts of water, followed by pulverization until the particle size reaches 5 microns or smaller.

FORMULATION EXAMPLE 8

A flowable is prepared by mixing 10 parts of compound A, B, C, D, E or F, 70 parts of 2,4-D, 3 parts of polyoxyethylene sorbitan monooleate, 3 parts of CMC (carboxymethylcellulose) and 14 parts of water, followed by pulverization until the particle size reaches 5 microns or smaller.

FORMULATION EXAMPLE 9

A wettable powder is prepared by well pulverizing and mixing 1 part of compound A, B, C, D, E or F. 50 parts of MCPA, 3 parts of calcium lignin sulfonate, 2 parts of sodium lauryl sulfate and 44 parts of synthetic hydrated silicon oxide.

FORMULATION EXAMPLE 10

A wettable powder is prepared by well pulverizing and mixing 13 parts of compound A, B, C, D, E or F, 65 parts of MCPA, 3 parts of calcium lignin sulfonate, 2 parts of sodium lauryl sulfate and 17 parts of synthetic hydrated silicon oxide.

FORMULATION EXAMPLE 11

A flowable is prepared by mixing 1 part of compound A, B, C, D, E or F, 50 parts of MCPA, 3 parts of polyoxyethylene sorbitan monooleate, 3 parts of CMC (carboxymethylcellulose) and 43 parts of water, followed by pulverization until the particle size reaches 5 microns or smaller.

FORMULATION EXAMPLE 12

A flowable is prepared by mixing 10 parts of compound A, B, C, D, E or F, 70 parts of MCPA, 3 parts of polyoxyethylene sorbitan monooleate, 3 parts of CMC (carboxymethylcellulose) and 14 parts of water, followed by pulverization until the particle size reaches 5 microns or smaller.

FORMULATION EXAMPLE 13

A wettable powder is prepared by well pulverizing and mixing 20 parts of compound A, B, C, D, E or F, 1 part of metsulfuron-methyl, 3 parts of calcium lignin sulfonate, 2 parts of sodium lauryl sulfate and 74 parts of synthetic hydrated silicon oxide.

FORMULATION EXAMPLE 14

A wettable powder is prepared by well pulverizing and mixing 13 parts of compound A, B, C, D, E or F, 65 parts of metsulfuron-methyl, 3 parts of calcium lignin sulfonate, 2 parts of sodium lauryl sulfate and 17 parts of synthetic hydrated silicon oxide.

FORMULATION EXAMPLE 15

A flowable is prepared by mixing 20 parts of compound A, B, C, D, E or F, 1 part of metsulfuron-methyl, 3 parts of polyoxyethylene sorbitan monooleate, 3 parts of CMC (carboxymethylcellulose) and 73 parts of water, followed by pulverization until the particle size reaches 5 microns or smaller.

FORMULATION EXAMPLE 16

A flowable is prepared by mixing 30 parts of compound A, B, C, D, E or F, 30 parts of metsulfuron-methyl, 3 parts of polyoxyethylene sorbitan monooleate, 3 parts of CMC (carboxymethylcellulose) and 34 parts of water, followed by pulverization until the particle size reaches 5 microns or smaller.

FORMULATION EXAMPLE 17

A wettable powder is prepared by well pulverizing and mixing 20 parts of compound A, B, C, D, E or F, 1 part of chlorsulfuron, 3 parts of calcium lignin sulfonate, 2 parts of sodium lauryl sulfate and 74 parts of synthetic hydrated silicon oxide.

FORMULATION EXAMPLE 18

A wettable powder is prepared by well pulverizing and mixing 13 parts of compound A, B, C, D, E or F, 65 parts of chlorsulfuron, 3 parts of calcium lignin sulfonate, 2 parts of sodium lauryl sulfate and 17 parts of synthetic hydrated silicon oxide.

FORMULATION EXAMPLE 19

A flowable is prepared by mixing 20 parts of compound A, B, C, D, E or F, 1 part of chlorsulfuron, 3 parts of polyoxyethylene sorbitan monooleate, 3 parts of CMC (carboxymethylcellulose) and 73 parts of water, followed by pulverization until the particle size reaches 5 microns or smaller.

FORMULATION EXAMPLE 20

A flowable is prepared by mixing 30 parts of compound A, B, C, D, E or F, 30 parts of chlorsulfuron, 3 parts of polyoxyethylene sorbitan monooleate, 3 parts of CMC (carboxymethylcellulose) and 34 parts of water, followed by pulverization until the particle size reaches 5 microns or smaller.

FORMULATION EXAMPLE 21

A wettable powder is prepared by well pulverizing and mixing 25 parts of compound A, B, C, D, E or F, 15 parts of fenoxaprop-P-ethyl, 3 parts of calcium lignin sulfonate, 2 parts of sodium lauryl sulfate and 55 parts of synthetic hydrated silicon oxide.

FORMULATION EXAMPLE 22

A wettable powder is prepared by well pulverizing and mixing 1 part of compound A, B, C, D, E or F. 70 parts of fenoxaprop-P-ethyl, 3 parts of calcium lignin sulfonate, 2 parts of sodium lauryl sulfate and 24 parts of synthetic hydrated silicon oxide.

FORMULATION EXAMPLE 23

A flowable is prepared by mixing 25 parts of compound A, B, C, D, E or F, 15 parts of fenoxaprop-P-ethyl, 3 parts of polyoxyethylene sorbitan monooleate, 3 parts of CMC (carboxymethylcellulose) and 54 parts of water, followed by pulverization until the particle size reaches 5 microns or smaller.

FORMULATION EXAMPLE 24

A flowable is prepared by mixing 1 part of compound A, B, C, D, E or F, 70 parts of fenoxaprop-P-ethyl, 3 parts of polyoxyethylene sorbitan monooleate, 3 parts of CMC (carboxymethylcellulose) and 23 parts of water, followed by pulverization until the particle size reaches 5 microns or smaller.

FORMULATION EXAMPLE 25

A wettable powder is prepared by well pulverizing and mixing 1 part of compound A, B, C, D, E or F. 50 parts of dichlofop-methyl, 3 parts of calcium lignin sulfonate, 2 parts of sodium lauryl sulfate and 44 parts of synthetic hydrated silicon oxide.

FORMULATION EXAMPLE 26

A wettable powder is prepared by well pulverizing and mixing 7 parts of compound A, B, C, D, E or F, 70 parts of dichlofop-methyl, 3 parts of calcium lignin sulfonate, 2 parts of sodium lauryl sulfate and 18 parts of synthetic hydrated silicon oxide.

FORMULATION EXAMPLE 27

A flowable is prepared by mixing 0.2 part of compound A, B, C, D, E or F, 40 parts of dichlofop-methyl, 3 parts of polyoxyethylene sorbitan monooleate, 3 parts of CMC (carboxymethylcellulose) and 53.8 parts of water, followed by pulverization until the particle size reaches 5 microns or smaller.

FORMULATION EXAMPLE 28

A flowable is prepared by mixing 3 parts of compound A, B, C, D, E or F, 30 parts of dichlofop-methyl, 3 parts of polyoxyethylene sorbitan monooleate, 3 parts of CMC (carboxymethylcellulose) and 61 parts of water, followed by pulverization until the particle size reaches 5 microns or smaller.

FORMULATION EXAMPLE 29

A wettable powder is prepared by well pulverizing and mixing 10 parts of compound A, B, C, D, E or F. 20 parts of bromoxynil, 3 parts of calcium lignin sulfonate, 2 parts of sodium lauryl sulfate and 65 parts of synthetic hydrated silicon oxide.

FORMULATION EXAMPLE 30

A wettable powder is prepared by well pulverizing and mixing 1 part of compound A, B, C, D, E or F, 70 parts of bromoxynil, 3 parts of calcium lignin sulfonate, 2 parts of sodium lauryl sulfate and 24 parts of synthetic hydrated silicon oxide.

FORMULATION EXAMPLE 31

A flowable is prepared by mixing 10 parts of compound A, B, C, D, E or F, 20 parts of bromoxynil, 3 parts of polyoxyethylene sorbitan monooleate, 3 parts of CMC (carboxymethylcellulose) and 64 parts of water, followed by pulverization until the particle size reaches 5 microns or smaller.

FORMULATION EXAMPLE 32

A flowable is prepared by mixing 1 part of compound A, B, C, D, E or F, 70 parts of bromoxynil, 3 parts of polyoxyethylene sorbitan monooleate, 3 parts of CMC (carboxymethylcellulose) and 23 parts of water, followed by pulverization until the particle size reaches 5 microns or smaller.

FORMULATION EXAMPLE 33

A wettable powder is prepared by well pulverizing and mixing 10 parts of compound A, B, C, D, E or F, 20 parts of ioxynil, 3 parts of calcium lignin sulfonate, 2 parts of sodium lauryl sulfate and 65 parts of synthetic hydrated silicon oxide.

FORMULATION EXAMPLE 34

A wettable powder is prepared by well pulverizing and mixing 1 part of compound A, B, C, D, E or F, 70 parts of ioxynil, 3 parts of calcium lignin sulfonate, 2 parts of sodium lauryl sulfate and 24 parts of synthetic hydrated silicon oxide.

FORMULATION EXAMPLE 35

A flowable is prepared by mixing 10 parts of compound A, B, C, D, E or F, 20 parts of ioxynil, 3 parts of polyoxyethylene sorbitan monooleate, 3 parts of CMC (carboxymethylcellulose) and 64 parts of water, followed by pulverization until the particle size reaches 5 microns or smaller.

FORMULATION EXAMPLE 36

A flowable is prepared by mixing 1 part of compound A, B, C, D, E or F, 70 parts of ioxynil, 3 parts of polyoxyethylene sorbitan monooleate, 3 parts of CMC (carboxymethylcellulose) and 23 parts of water, followed by pulverization until the particle size reaches 5 microns or smaller.

FORMULATION EXAMPLE 37

A wettable powder is prepared by well pulverizing and mixing 1 part of compound A, B, C, D, E or F, 50 parts of isoproturon, 3 parts of calcium lignin sulfonate, 2 parts of sodium lauryl sulfate and 44 parts of synthetic hydrated silicon oxide.

FORMULATION EXAMPLE 38

A wettable powder is prepared by well pulverizing and mixing 7 parts of compound A, B, C, D, E or F, 70 parts of isoproturon, 3 parts of calcium lignin sulfonate, 2 parts of sodium lauryl sulfate and 18 parts of synthetic hydrated silicon oxide.

FORMULATION EXAMPLE 39

A flowable is prepared by mixing 1 part of compound A, B, C, D, E or F, 50 parts of isoproturon, 3 parts of polyoxyethylene sorbitan monooleate, 3 parts of CMC (carboxymethylcellulose) and 43 parts of water, followed by pulverization until the particle size reaches 5 microns or smaller.

FORMULATION EXAMPLE 40

A flowable is prepared by mixing 7 parts of compound A, B, C, D, E or F, 70 parts of isoproturon, 3 parts of polyoxyethylene sorbitan monooleate, 3 parts of CMC (carboxymethylcellulose) and 17 parts of water, followed by pulverization until the particle size reaches 5 microns or smaller.

FORMULATION EXAMPLE 41

A wettable powder is prepared by well pulverizing and mixing 0.2 part of compound A, B, C, D, E or F; 50 parts of chlorotoluron, 3 parts of calcium lignin sulfonate, 2 parts of sodium lauryl sulfate and 44.8 parts of synthetic hydrated silicon oxide.

FORMULATION EXAMPLE 42

A wettable powder is prepared by well pulverizing and mixing 3 parts of compound A, B, C, D, E or F, 70 parts of chlorotoluron, 3 parts of calcium lignin sulfonate, 2 parts of sodium lauryl sulfate and 22 parts of synthetic hydrated silicon oxide.

FORMULATION EXAMPLE 43

A flowable is prepared by mixing 0.2 part of compound A, B, C, D, E or F, 50 parts of chlorotoluron, 3 parts of polyoxyethylene sorbitan monooleate, 3 parts of CMC (carboxymethylcellulose) and 43.8 parts of water, followed by pulverization until the particle size reaches 5 microns or smaller.

FORMULATION EXAMPLE 44

A flowable is prepared by mixing 3 parts of compound A, B, C, D, E or F, 70 parts of chlorotoluron, 3 parts of polyoxyethylene sorbitan monooleate, 3 parts of CMC (carboxymethylcellulose) and 21 parts of water, followed by pulverization until the particle size reaches 5 microns or smaller.

FORMULATION EXAMPLE 45

A wettable powder is prepared by well pulverizing and mixing 20 parts of compound A, B, C, D, E or F; 20 parts of diflufenican, 3 parts of calcium lignin sulfonate, 2 parts of sodium lauryl sulfate and 55 parts of synthetic hydrated silicon oxide.

FORMULATION EXAMPLE 46

A wettable powder is prepared by well pulverizing and mixing 1 part of compound A, B, C, D, E or F, 70 parts of diflufenican, 3 parts of calcium lignin sulfonate, 2 parts of sodium lauryl sulfate and 24 parts of synthetic hydrated silicon oxide.

FORMULATION EXAMPLE 47

A flowable is prepared by mixing 20 parts of compound A, B, C, D, E or F, 20 parts of diflufenican, 3 parts of polyoxyethylene sorbitan monooleate, 3 parts of CMC (carboxymethylcellulose) and 54 parts of water, followed by pulverization until the particle size reaches 5 microns or smaller.

FORMULATION EXAMPLE 48

A flowable is prepared by mixing 1 part of compound A, B, C, D, E or F, 60 parts of diflufenican, 3 parts of polyoxyethylene sorbitan monooleate, 3 parts of CMC (carboxymethylcellulose) and 33 parts of water, followed by pulverization until the particle size reaches 5 microns or smaller.

FORMULATION EXAMPLE 49

A flowable is prepared by mixing 1 part of compound A, B, C, D, E or F, 12 parts of diflufenican, 3 parts of polyoxyethylene sorbitan monooleate, 3 parts of CMC (carboxymethylcellulose) and 81 parts of water, followed by pulverization until the particle size reaches 5 microns or smaller.

The following will describe Test Examples.

Criteria of Evaluation

The herbicidal activity is classified at 11 levels extending from "0" to "10" and evaluated by "0", "1", "2", "3", "4", "5", "6", "7", "8", "9" or "10", in which the level "0" indicates no or little difference in the state of germination or growth of test weeds at the time of examination as compared with that of untreated weeds and the level "10" indicates complete death of test weeds or complete inhibition of their germination or growth. For evaluated values of herbicidal activity, the level "7", "8", "9", or "10" means excellent herbicidal activity, whereas the level "6" or lower means insufficient herbicidal activity. The phytotoxicity is evaluated by "no damage" when little phytotoxicity is observed, by "light" when slight phytotoxicity is observed, by "medium" when moderate phytotoxicity is observed, or by "heavy" when serious phytotoxicity is observed.

TEST EXAMPLE 1

Cylindrical plastic pots of 10 cm in diameter and 10 cm in depth were filled with field soil, and seeded with wheat and blackgrass. These test plants were grown in a greenhouse.

A flowable of compound A obtained by mixing 5 parts of compound A, 50 parts of 10% aqueous polyvinyl alcohol solution and 45 parts of water, and pulverizing the mixture until the particle size reached 5 microns or smaller; a formulated product of mecoprop (trade name, MCPP; Riken); a formulated product of metsulfuron-methyl (trade name, Ally; Du Pont); a formulated product of fenoxaprop-P-ethyl (trade name, Pumas; Hoechst); a formulated product of bromoxynil (trade name, Buctril; Rhone Poulenc); a formulated product of isoproturon (trade name, Arelon; Hoechst-Schering); a flowable of diflufenican obtained by mixing 25 parts of diflufenican, 50 parts of 10% aqueous polyvinyl alcohol solution and 25 parts of water, and pulverizing the mixture until the particle size reached 5 microns or smaller; a mixed formulation of the flowable of compound A and the formulated product of mecoprop; a mixed formulation of the flowable of compound A and the formulated product of metsulfuron-methyl; a mixed formulation of the flowable of compound A and the formulated product of fenoxaprop-P-ethyl; a mixed formulation of the flowable of compound A and the formulated product of bromoxynil; a mixed formulation of the flowable of compound A and the formulated product of isoproturon; or a flowable of a mixed formulation of compound A and diflufenican, which had been formulated according to Formulation Example 49, was diluted in each prescribed amount with water, and uniformly sprayed over the foliage of the test plants with a small sprayer. For compound B, the same test was carried out. After the treatment, the test plants were grown in the greenhouse for 4 days, and the herbicidal activity and the safety on wheat were examined. The results are shown in Table 2.

TABLE 2

| Compound | Application dose (g/ha) | Herbicidal activity blackgrass | Phytotoxicity wheat |
| --- | --- | --- | --- |
| Compound A | 10 | 3 | no damage |
| Compound B | 10 | 3 | no damage |
| Mecoprop | 2000 | 0 | no damage |
| Metsulfuron-methyl | 6 | 0 | no damage |
| Fenoxaprop-P-ethyl | 80 | 2 | no damage |
| Bromoxynil | 300 | 0 | no damage |
| Isoproturon | 1500 | 0 | no damage |
| Diflufenican | 120 | 1 | no damage |
| Compound A + mecoprop | 10 + 2000 | 8 | no damage |
| Compound B + mecoprop | 10 + 1500 | 8 | no damage |
| Compound A + metsulfuron-methyl | 10 + 6 | 7 | no damage |
| Compound B + metsulfuron-methyl | 10 + 6 | 7 | no damage |
| Compound A + fenoxaprop-P-ethyl | 10 + 80 | 9 | no damage |
| Compound B + fenoxaprop-P-ethyl | 10 + 80 | 9 | no damage |
| Compound A + bromoxynil | 10 + 300 | 8 | no damage |
| Compound B + bromoxynil | 10 + 300 | 8 | no damage |
| Compound A + isoproturon | 10 + 1500 | 8 | no damage |
| Compound B + isoproturon | 10 + 1500 | 8 | no damage |
| Compound A + diflufenican | 10 + 120 | 7 | no damage |
| Compound B + diflufenican | 10 + 120 | 7 | no damage |

TEST EXAMPLE 2

Cylindrical plastic pots of 17 cm in diameter and 14.5 cm in depth were filled with field soil, and seeded with giant foxtail, barnyardgrass and annual bluegrass. These test plants were grown in a greenhouse for 42 days in the case of giant foxtail and for 31 days in the cases of barnyardgrass and annual bluegrass.

A flowable of compound A obtained by mixing 5 parts of compound A, 50 parts of 10% aqueous polyvinyl alcohol solution and 45 parts of water, and pulverizing the mixture until the particle size reached 5 microns or smaller; a formulated product of mecoprop (trade name, MCPP; Riken); a formulated product of metsulfuron-methyl (trade name, Ally; Du Pont); a formulated product of bromoxynil (trade name, Buctril; Phone Polenc); a formulated product of isoproturon (trade name, Arelon; Hoechst-Schering); a mixed formulation of the flowable of compound A and the formulated product of mecoprop; a mixed formulation of the flowable of compound A and the formulated product of metsulfuron-methyl; a mixed formulation of the flowable of compound A and the formulated product of bromoxynil; or a mixed formulation of the flowable of compound A and the formulated product of isoproturon was diluted in each prescribed amount with water, and uniformly sprayed over the foliage of the test plants with a small sprayer. After the treatment, the test plants were grown in the greenhouse for 4 days, and the herbicidal activity was examined. The results are shown in Table 3.

TABLE 3

| Compound | Application dose (g/ha) | Herbicidal activity | | |
|---|---|---|---|---|
| | | giant foxtail | barnyard-grass | annual bluegrass |
| Compound A | 10 | 4 | 5 | 6 |
| Mecoprop | 2000 | 0 | 2 | 1 |
| Metsulfuron-methyl | 6 | 1 | 0 | 0 |
| Bromoxynil | 6 | 1 | 0 | 1 |
| Isoproturon | 1000 | 1 | 2 | 0 |
| Compound A + mecoprop | 10 + 2000 | 8 | 9 | 8 |
| Compound A + metsulfuron-methyl | 10 + 6 | 7 | 8 | 9 |
| Compound A + bromoxynil | 10 + 6 | 9 | 9 | 8 |
| Compound A + isoproturon | 10 + 1000 | 7 | 9 | 9 |

TEST EXAMPLE 3

Cylindrical plastic pots of 17 cm in diameter and 14.5 cm in depth were filled with field soil, and seeded with giant foxtail and barnyardgrass. These test plants were grown in a greenhouse for 42 days in the case of giant foxtail and for 31 days in the case of barnyardgrass.

A flowable of compound A obtained by mixing 5 parts of compound A, 50 parts of 10% aqueous polyvinyl alcohol solution and 45 parts of water, and pulverizing the mixture until the particle size reached 5 microns or smaller; a formulated product of fenoxaprop-P-ethyl (trade name, Pumas; Hoechst); or a mixed formulation of the flowable of compound A and the formulated product of fenoxaprop-P-ethyl was diluted in each prescribed amount with water, and uniformly sprayed over the foliage of the test plants with a small sprayer. After the treatment, the test plants were grown in the greenhouse for 4 days, and the herbicidal activity was examined. The results are shown in Table 4.

TABLE 4

| Compound | Application dose (g/ha) | Herbicidal activity | |
|---|---|---|---|
| | | giant foxtail | barnyard-grass |
| Compound A | 10 | 4 | 5 |
| Fenoxaprop-P-ethyl | 80 | 4 | 3 |
| Compound A + fenoxaprop-P-ethyl | 10 + 80 | 10 | 9 |

TEST EXAMPLE 4

Cylindrical plastic pots of 17 cm in diameter and 14.5 cm in depth were filled with field soil, and seeded with barnyardgrass and annual bluegrass. These test plants were grown in a greenhouse for 31 days.

A flowable of compound A obtained by mixing 5 parts of compound A, 50 parts of 10% aqueous polyvinyl alcohol solution and 45 parts of water, and pulverizing the mixture until the particle size reached 5 microns or smaller; a flowable of diflufenican obtained by mixing 26 parts of diflufenican, 50 parts of 10% aqueous polyvinyl alcohol solution and 25 parts of water, and pulverizing the mixture until the particle size reached 5 microns or smaller; or a flowable of a mixed formulation of compound A and diflufenican, which had been formulated according to Formulation Example 49, was diluted in each prescribed amount with water, and uniformly sprayed over the foliage of the test plants with a small sprayer. After the treatment, the test plants were grown in the greenhouse for 4 days, and the herbicidal activity was examined. The results are shown in Table 5.

TABLE 5

| Compound | Application dose (g/ha) | Herbicidal activity | |
|---|---|---|---|
| | | barnyard-grass | annual bluegrass |
| Compound A | 10 | 5 | 6 |
| Diflufenican | 120 | 0 | 0 |
| Compound A + diflufenican | 10 + 120 | 7 | 8 |

A wide variety of weeds such as those on fields, particularly on wheat, barley, oat, or rye fields, can be selectively controlled with the present compositions.

What is claimed is:

1. A herbicide composition for foliar treatment, characterized in that it comprises as active ingredients, a 2-chloro-4-fluoro-5-(4-methyl-5trifluoromethyl-3-pyridazinon-2-yl) phenyl $C_1$–$C_5$ non-cyclic hydrocarbyl ether and one selected from the group consisting of (RS)-2-(4-chloro-2-methylphenoxy)propionic acid, 2,4-dichlorophenoxyacetic acid, (4-chloro-2-methyl)phenoxyacetic acid, 2-[[[[(4-methoxy-6-methyl- 1,3,5-triazin-2-yl)-amino]carbonyl] amino]sulfonyl]benzoate, 2-chloro-N- [[(4-methoxy-6-methyl- 1,3,5triazin-2-yl)amino]carbonyl] benzenesulfonamide, ethyl (R)-2-[4-(6-chloro1,3-benzoxazol-2-yloxy)phenoxy]propanoate, methyl (RS)-2-[4-(2,4-dichlorophenoxy)phenoxy]propionate, 3,5-dibromo-4-hydroxybenzonitrile, 4-hydroxy3,5-diiodobenzonitrile, 3-(4-isopropylphenyl)-N',N'-dimethylurea, N'-(3chloro-4-methylphenyl)-N,N-dimethylurea and N-(2,4-difluorophenyl)-2-[3(trifluoromethyl)phenoxy]-3-pyridinecarboxamide.

2. The herbicide composition according to claim 1, characterized in that it comprises as active ingredients, a 2-chloro-4-fluoro-5-(4-methyl-5trifluoromethyl-3-pyridazinon-2-yl)phenyl $C_1$–$C_5$ non-cyclic hydrocarbyl ether and one selected from the group consisting of (RS)-2-(4-chloro-2-methylphenoxy)propionic acid, 2,4-dichlorophenoxyacetic acid and (4-chloro-2methyl)phenoxyacetic acid.

3. The herbicide composition according to claim 2, wherein the weight ratio of the 2-chloro-4-fluoro-5-(4-methyl-5-trifluoromethyl-3pyridazinon-2-yl)phenyl $C_1$–$C_5$ non-cyclic hydrocarbyl ether and one selected from the group consisting of (RS)-2-(4-chloro-2-methylphenoxy)propionic acid, 2,4-dichlorophenoxyacetic acid and (4-chloro-2-methyl)phenoxyacetic acid is in the range of 1:5 to 1000.

4. The herbicide composition according to claim 1, characterized in that it comprises as active ingredients, a 2-chloro-4-fluoro-5-(4-methyl-5trifluoromethyl-3-pyridazinon-2-yl)phenyl $C_1$–$C_5$ non-cyclic hydrocarbyl ether and one selected from the group consisting of 2-[[[[(4-methoxy-6-methyl1,3,5-triazin-2-yl)-amino]carbonyl]amino]sulfonyl] benzoate and 2-chloro-N[[(4-methoxy-6-methyl-1,3,5-triazin-2-yl)amino]carbonyl]benzenesulfonamide.

5. The herbicide composition according to claim 4, wherein the weight ratio of the 2-chloro-4-fluoro-5-(4-methyl-5-trifluoromethyl-3pyridazinon-2-yl)phenyl $C_1$–$C_5$ non-cyclic hydrocarbyl ether and one selected from the group consisting of 2-[[[[(4-methoxy-6-methyl-1,3,5-triazin-2-yl)amino)carbonyl]amino]sulfonyl] benzoate and 2-chloro-N-[[(4-methoxy-6methyl-1,3,5-triazin-2-yl)amino]carbonyl]benzenesulfonamide is in the range of 1:0.05 to 5.

6. The herbicide composition according to claim 1, characterized in that it comprises as active ingredients, a 2-chloro-4-fluoro-5-(4-methyl-5trifluoromethyl-3-pyridazinon-2-yl)phenyl $C_1$–$C_5$ non-cyclic hydrocarbyl ether and one selected from the group consisting of ethyl (R)-2-[4-(6-chloro-1,3benzoxazol-2-yloxy)phenoxy] propanoate and methyl (RS)-2-[4-(2,4-dichlorophenoxy)phenoxy]propionate.

7. The herbicide composition according to claim 6, wherein the weight ratio of the 2-chloro-4-fluoro-5-(4-methyl-5-trifluoromethyl-3pyridazinon-2-yl)phenyl $C_1$–$C_5$ non-cyclic hydrocarbyl ether and one selected from the group consisting of ethyl (R)-2-[4-(6-chloro-1,3-benzoxazol-2-yloxy)5 phenoxy]propanoate and methyl (RS)-2-[4-(2,4-dichlorophenoxy)phenoxy]propionate is in the range of 1:0.5 to 1000.

8. The herbicide composition according to claim 1, characterized in that it comprises as active ingredients, a 2-chloro-4-fluoro-5-(4-methyl-5trifluoromethyl-3-pyridazinon-2-yl)phenyl $C_1$–$C_5$ non-cyclic hydrocarbyl ether and one selected from the group consisting of 3,5-dibromo-4-hydroxybenzonitrile and 4-hydroxy-3,5-diiodobenzonitrile.

9. The herbicide composition according to claim 8, wherein the weight ratio of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of 3,5-dibromo-4-hydroxybenzonitrile and 4-hydroxy-3,5-diiodobenzonitrile is in the range of 1:0.6 to 200.

10. The herbicide composition according to claim 1, characterized in that it comprises as active ingredients, a 2-chloro-4-fluoro-5-(4-methyl-5trifluoromethyl-3-pyridazinon-2-yl)phenyl $C_1$–$C_5$ non-cyclic hydrocarbyl ether and one selected from the group consisting of 3-(4-isopropylphenyl)-N',N'-dimethylurea and N'-(3-chloro-4-methylphenyl)-N,N-dimethylurea.

11. The herbicide composition according to claim 10, wherein the weight ratio of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of 3-(4-isopropylphenyl)-N',N'-dimethylurea and N'-(3-chloro-4-methylphenyl)-N,N-dimethylurea is in the range of 1:10 to 2000.

12. The herbicide composition according to claim 1, characterized in that it comprises as active ingredients, a 2-chloro-4-fluoro-5-(4-methyl-5trifluoromethyl-3-pyridazinon-2-yl)phenyl $C_1$–$C_5$ non-cyclic hydrocarbyl ether and N-(2,4-difluorophenyl)-2-[3-(trifluoromethyl)phenoxy]-3-pyridinecarboxamide.

13. The herbicide composition according to claim 12, wherein the weight ratio of the 2-chloro-4-fluoro-5-(4-methyl-5-trifluoromethyl-3-pyridazinon-2-yl)phenyl $C_1$—$C_5$ non-cyclic hydrocarbyl ether and N-(2,4-difluorophenyl)-2-[3-(trifluoromethyl)phenoxy]-3-pyridinecarbox amide is in the range of 1:1 to 100.

14. A weeding method characterized in that it comprises foliar treatment of weeds with a herbicide containing as active ingredients, a 2-chloro-4-fluoro- 5-(4-methyl-5-trifluoromethyl- 3-pyridazinon-2-yl)phenyl $C_1$–$C_5$ non-cyclic hydrocarbyl ether and one selected from the group consisting of (RS)-2-(4-chloro-2-methylphenoxy)propionic acid, 2,4-dichlorophenoxyacetic acid, (4-chloro-2-methyl)phenoxyacetic acid, 2-[[[[(4-methoxy-6-methyl-1,3,5-triazin-2-yl)-amino]carbonyl]amino]sulfonyl] benzoate, 2-chloro-N[[(4-methoxy-6-methyl-1,3,5-triazin-2-yl)amino]carbonyl]benzenesulfonamide, ethyl (R)-2-[4-(6-chloro-1,3-benzoxazol-2-yloxy)phenoxy]propanoate, methyl (RS)-2-[4-(2,4-dichlorophenoxy)phenoxy] propionate, 3,5-dibromo-4hydroxybenzonitrile, 4-hydroxy-3,5-diiodobenzonitrile, 3-(4-isopropylphenyl)-N',N'-dimethylurea, N'-(3-chloro-4-methylphenyl)-N,N-dimethylurea and N-(2,4-difluorophenyl)-2-[13-(trifluoromethyl)phenoxy]-3-pyridinecarbox amide.

15. The weeding method according to claim 14, wherein the herbicide is applied to weeds on wheat, barley, oat, or rye fields.

16. The weeding method according to claim 14, characterized in that it comprises foliar treatment of weeds with a herbicide containing as active ingredients, a 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of (RS)-2-(4-chloro-2-methylphenoxy)propionic acid, 2,4dichlorophenoxyacetic acid and (4-chloro-2-methyl)phenoxyacetic acid.

17. The weeding method according to claim 16, wherein the herbicide is applied to weeds on wheat, barley, oat, or rye fields.

18. The weeding method according to claim 16 or 17; wherein the weight ratio of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of (RS)-2-(4-chloro-2-methylphenoxy)propionic acid, 2,4dichlorophenoxyacetic acid and (4-chloro-2-methyl)phenoxyacetic acid is in the range of 1:5 to 1000.

19. The weeding method according to claim 18 wherein the total amount of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of (RS)-2-(4-chloro-2-methylphenoxy)propionic acid, 2,4dichlorophenoxyacetic acid and (4-chloro-2-methyl)phenoxyacetic acid is 2 to 2500 g per hectare.

20. The weeding method according to claim 16 or 17, wherein the total amount of the 2-chloro-4-fluoro-5-(4-methyl-5-trifluoromethyl-320 pyridazinon-2-yl)phenyl $C_1$–$C_5$ non-cyclic hydrocarbyl ether and one selected from the group consisting of (RS)-2-(4-chloro-2-methylphenoxy) propionic acid, 2,4-dichlorophenoxyacetic acid and (4-chloro-2-methyl)phenoxyacetic acid is 2 to 2500 g per hectare.

21. The weeding method according to claim 14, characterized in that it comprises foliar treatment of weeds with a herbicide containing as active ingredients, a 2-chloro-4-fluoro-5-(4-methyl-5-trifluoromethyl-3-pyridazinon-2-yl) phenyl $C_1$–$C_5$ non-cyclic hydrocarbyl ether and one selected from the group consisting of 2-[[[[(4-methoxy-6-methyl-1,3,5-triazin-2-yl)-amino]-carbonyl]amino]sulfonyl] benzoate, and 2-chloro-N-[[(4-methoxy-6-methyl1,3,5-triazin-2-yl)amino]carbonyl]benzenesulfonamide.

22. The weeding method according to claim 21, wherein the herbicide is applied to weeds on wheat, barley, oat, or rye fields.

23. The weeding method according to claim 21 or 22, wherein the weight ratio of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of 2-[[[[(4-methoxy-6-methyl-1,3,5-triazin-2-yl)-amino]-carbonyl]amino]sulfonyl] benzoate and 2-chloro-N-[[(4-methoxy-6-methyl1,3,5-triazin-2-yl) amino]carbonyl]benzenesulfonamide is in the range of 1:0.05 to 5.

24. The weeding method according to claim 23 wherein the total amount of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of 2-[[[[(4-methoxy-6-methyl-1,3,5-triazin-2-yl)-amino]-carbonyl]amino]sulfonyl] benzoate and 2-chloro-N-[[(4-methoxy-6-methyl1,3,5-triazin-2-yl)amino]carbonyl] benzenesulfonamide is 2 to 100 g per hectare.

25. The weeding method according to claim 21 or 22, wherein the total amount of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of 2-[[[[(4-methoxy-6-methyl-1,3,5-triazin-2-yl)amino]carbonyl]amino]sulfonyl] benzoate and 2-chloro-N-[[(4-methoxy-6methyl-1,3,5-triazin-2-yl) amino]carbonyl]benzenesulfonamide is 2 to 100 g per hectare.

26. The weeding method according to claim 14, characterized in that it comprises foliar treatment of weeds with a herbicide containing as active ingredients, a 2-chloro-4-fluoro-5-(4-methyl-5-trifluoromethyl-3-pyridazinon-2-yl) phenyl $C_1$–$C_5$ non-cyclic hydrocarbyl ether and one selected from the group consisting of ethyl (R)-2-[4-(6-chloro-1,3-benzoxazol-2-yloxy)phenoxy]propanoate and methyl (RS)-2-[4-(2,4-dichlorophenoxy)phenoxy]-propionate.

27. The weeding method according to claim 26, wherein the herbicide is applied to weeds on wheat, barley, oat, or rye fields.

28. The weeding method according to claim 26 or 27, wherein the weight ratio of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of ethyl (R)-2-[4-(6-chloro-1,3-benzoxazol-2-yloxy)phenoxy]propanoate and methyl (RS)-2-[4-(2,4-dichlorophenoxy)phenoxy]propionate is in the range of 1:0.5 to 1000.

29. The weeding method according to claim 28 wherein the total amount of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of ethyl (R)-2-[4-(6-chloro-1,3-benzoxazol-2-yloxy)phenoxy]propanoate and methyl (RS)-2-[4-(2,4-dichlorophenoxy)phenoxy]propionate is 2 to 1000 g per hectare.

30. The weeding method according to claim 26 or 27, wherein the total amount of the 2-chloro-4-fluoro-5-(4-methyl-5-trifluoromethyl-3pyridazinon-2-yl)phenyl $C_1$–$C_5$ non-cyclic hydrocarbyl ether and one selected from the group consisting of ethyl (R)-2-[4-(6-chloro-1,3-benzoxazol-2-yloxy)phenoxy]propanoate and methyl (RS)-2-[4-(2,4-dichlorophenoxy)phenoxy]propionate is 2 to 1000 g per hectare.

31. The weeding method according to claim 14, characterized in that it comprises foliar treatment of weeds with a herbicide containing as active ingredients, a 2-chloro-4-fluoro-5-(4-methyl-5-trifluoromethyl-3-pyridazinon-2-yl) phenyl $C_1$–$C_5$ non-cyclic hydrocarbyl ether and one selected from the group consisting of 3,5-dibromo-4-hydroxybenzonitrile and 4-hydroxy3,5-diiodobenzonitrile.

32. The weeding method according to claim 31, wherein the herbicide is applied to weeds on wheat, barley, oat, or rye fields.

33. The weeding method according to claim 31 or 32, wherein the weight ratio of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of 3,5-dibromo-4-hydroxybenzonitrile and 4-hydroxy3,5-diiodobenzonitrile is in the range of 1:0.6 to 200.

34. The weeding method according to claim 33 wherein the total amount of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of 3,5-dibromo-4-hydroxybenzonitrile and 4-hydroxy3,5-diiodobenzonitrile is 2 to 500 g per hectare.

35. The weeding method according to claim 31 or 32, wherein the total amount of the 2-chloro-4-fluoro-5-(4-methyl-5-trifluoromethyl-3pyridazinon-2-yl)phenyl $C_1$–$C_5$ non-cyclic hydrocarbyl ether and one selected from the group consisting of 3,5-dibromo-4-hydroxybenzonitrile and 4-hydroxy-3,5-diiodobenzonitrile is 2 to 500 g per hectare.

36. The weeding method according to claim 14, characterized in that it comprises foliar treatment of weeds with a herbicide containing as active ingredients, a 2-chloro-4-fluoro-5-(4-methyl-5-trifluoromethyl-3-pyridazinon-2-yl) phenyl $C_1$–$C_5$ non-cyclic hydrocarbyl ether and one selected from the group consisting of 3-(4-isopropylphenyl)-N',N'-dimethylurea and N'-(3chloro-4-methylphenyl)-N,N-dimethylurea.

37. The weeding method according to claim 36, wherein the herbicide is applied to weeds on wheat, barley, oat, or rye fields.

38. The weeding method according to claim 36 or 37, wherein the weight ratio of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of 3-(4-isopropylphenyl)-N',N'-dimethylurea and N'-(3chloro-4-methylphenyl)-N,N-dimethylurea is in the range of 1:10 to 2000.

39. The weeding method according to claim 38 wherein the total amount of the 2-chloro-4-fluoro-5-(4-methyl-5-trifluoromethyl-3-pyridazinon-2-yl)phenyl $C_1$–$C_5$ non-cyclic hydrocarbyl ether and one selected from the group consisting of 3-(4-isopropylphenyl)-N',N'-dimethylurea and N'-(3chloro-4-methylphenyl)-N,N-dimethylurea is 2 to 2500 g per hectare.

40. The weeding method according to claim 36 or 37, wherein the total amount of the 2-chloro-4-fluoro-5-(4-methyl-5-trifluoromethyl-3pyridazinon-2-yl)phenyl $C_1$–$C_5$ non-cyclic hydrocarbyl ether and one selected from the group consisting of 3-(4-isopropylphenyl)-N',N'-dimethylurea and N'-(3-chloro-4-methylphenyl)-N,N-dimethylurea is 2 to 2500 g per hectare.

41. The weeding method according to claim 14, characterized in that it comprises foliar treatment of weeds with a herbicide containing as active ingredients, a 2-chloro-4-fluoro-5-(4-methyl-5-trifluoromethyl-3-pyridazinon-2-yl)phenyl $C_1$–$C_5$ non-cyclic hydrocarbyl ether and N-(2,4-difluorophenyl)-2-[3-(trifluoromethyl)phenoxy]-3-pyridinecarboxamide.

42. The weeding method according to claim 41, wherein the herbicide is applied to weeds on wheat, barley, oat, or rye fields.

43. The weeding method according to claim 41 or 42, wherein the weight ratio of the 2-chloro-4-fluoro-5-(4-methyl-5-trifluoromethyl-3-pyridazinon-2-yl)phenyl $C_1$–$C_5$ non-cyclic hydrocarbyl ether and N-(2,4-difluorophenyl)-2-[3-(trifluoromethyl)phenoxy]-3-pyridinecarboxamide is in the range of 1:1 to 100.

44. The weeding method according to claim 43 wherein the total amount of the 2-chloro-4-fluoro-5-(4-methyl-5-trifluoromethyl-3-pyridazinon-2-yl)phenyl $C_1$–$C_5$ non-cyclic hydrocarbyl ether and N-(2,4-difluorophenyl)-2-[3-(trifluoromethyl)phenoxy]-3-pyridinecarboxamide is 2 to 200 g per hectare.

45. The weeding method according to claim 41 or 42, wherein the total amount of the 2-chloro-4-fluoro-5-(4-methyl-5-trifluoromethyl-3pyridazinon-2-yl)phenyl $C_1$–$C_5$ non-cyclic hydrocarbyl ether and N-(2,4-difluorophenyl)-2-[3-(trifluoromethyl)phenoxy]-3-pyridinecarboxamide is 2 to 200 g per hectare.

* * * * *